(12) United States Patent
Dickinson et al.

(10) Patent No.: US 7,018,657 B2
(45) Date of Patent: Mar. 28, 2006

(54) PARTICULATE COMPOSITION

(75) Inventors: Paul Alfred Dickinson, Macclesfield (GB); Ian Walter Kellaway, Cardiff (GB); Stephen Wyn Howells, Cardiff (GB)

(73) Assignee: University College Cardiff Consultants Limited, Cardiff (GB)

( * ) Notice: Subject to any disclaimer, the term of this patent is extended or adjusted under 35 U.S.C. 154(b) by 186 days.

(21) Appl. No.: 10/258,190

(22) PCT Filed: Apr. 18, 2001

(86) PCT No.: PCT/GB01/01752

§ 371 (c)(1),
(2), (4) Date: Jan. 17, 2003

(87) PCT Pub. No.: WO01/78689

PCT Pub. Date: Oct. 25, 2001

(65) Prior Publication Data

US 2003/0161886 A1    Aug. 28, 2003

(30) Foreign Application Priority Data

Apr. 19, 2000    (GB) .................................. 0009773

(51) Int. Cl.
*A61K 9/14*    (2006.01)
*A61K 9/12*    (2006.01)
*A61K 9/127*    (2006.01)

(52) U.S. Cl. ...................... 424/489; 424/498; 424/499; 424/495; 424/45; 424/46

(58) Field of Classification Search ................ 424/489, 424/498, 499, 495, 45, 46
See application file for complete search history.

(56) References Cited

U.S. PATENT DOCUMENTS

| | | | |
|---|---|---|---|
| 5,091,188 A | | 2/1992 | Haynes ........................ 424/450 |
| 5,145,684 A | * | 9/1992 | Liversidge et al. .......... 424/489 |
| 5,223,244 A | * | 6/1993 | Moro et al. .................... 424/46 |
| 6,245,319 B1 | * | 6/2001 | Quay .......................... 424/9.52 |
| 6,309,623 B1 | * | 10/2001 | Weers et al. ................... 424/45 |
| 6,811,767 B1 | * | 11/2004 | Bosch et al. .................. 424/45 |

FOREIGN PATENT DOCUMENTS

| | | |
|---|---|---|
| EP | 0 526 666 A1 | 2/1993 |
| EP | 0 274 431 B1 | 5/1994 |
| EP | 0 877 033 A1 | 11/1998 |
| WO | WO 93/00076 | 1/1993 |
| WO | WO 96/25919 | 8/1996 |
| WO | WO 97/20041 | 6/1997 |

OTHER PUBLICATIONS

Database WPI, Section Ch, week 198915, AN 1989-110408 & JP 01056136.
Howells S.W. et al.: "Novel Nanoparticles from Windsor II AOT Microemulsions" Proc. Symp. On "Lipid and Surfactant and Dispersed Systems" Moscow Sep. 26-28, 1999 181-182.
Howells S.W., et al.: "Novel Nanoparticles from Inverted Micelles for Drug Delivery" Proc. 6th Annual Ukaps Conf. Jun. 28-30, Manchester (1999) 2.
E. Merisko-Liversidge, et al.; "Nanosizing: a formulation approach for poorly-water-soluble compounds"; European Journal of Pharmaceutical Sciences 18 (2003) pp. 113-120.

* cited by examiner

*Primary Examiner*—Sreeni Padmanabhan
*Assistant Examiner*—Mina Haghighatian
(74) *Attorney, Agent, or Firm*—Darby & Darby (57) ABSTRACT

Nanoparticles are prepared from a colloidal system comprising a continuous phase and micelles, the micelles comprising surfactant material. A microemulsion is formed by admixing the colloidal system with a solution of an active material, such as a medicament, dissolved in a solvent wherein the solution forms a disperse phase with the micelles of surfactant material. At least the dispersed phase is quenched to a solid state and the continuous phase and solvent are removed to produce the nanoparticles. The nanoparticles can be incorporated in an aerosol composition suitable for deep lung delivery by means of a metered dose inhaler.

20 Claims, 3 Drawing Sheets

FIG. 1

Ternary Plot

— Phase Boundary

FIG. 2

FIG. 3

Lecithin:Propan-2-ol (1:3)

—●— Phase Boundary Line

PARTICULATE COMPOSITION

CROSS REFERENCE TO RELATED APPLICATIONS

This application is a National Stage under 35 U.S.C. §371 of PCT International Application No. PCT/GB01/01752 filed Apr. 18, 2001, which claims benefit under 35 U.S.C. §119(e) of Great Britain Application No. 0009773.3 filed Apr. 19, 2000, the entire contents of which are incorporated herein by reference. The International Appplication was published in English on Oct. 25, 2001 as WO 01/78689 under PCT Article 21(2).

The present invention relates to a particulate composition and to a method for preparing a particulate composition. Particularly, but not exclusively, the present invention also relates to an aerosol composition including the present particulate composition and to the use of such an aerosol composition in administering a medicament, for example, for treating a respiratory disease.

There have been a number of proposals to provide particulate compositions comprising so-called nanoparticles. "Nanoparticles" are particles whose average dimension lies within the range of from 1 nm to up to, but not including, 1000 nm.

EP-A-0526666 describes a process for preparing solid lipid microspheres having an average diameter lower than one micron. The process comprises forming a microemulsion comprising a molten lipid, which may contain a drug, and a mixture of water and surfactant, dispersing the microemulsion in water at a temperature of between 2 and 10° C., washing the lipid microspheres obtained with water through diafiltration to remove the surfactant and any free drug, and lyophilising.

WO 93/00076 describes nanoparticles as a carrier system for drugs. The particles are formed from a biopolymer by desolvation, thermal denaturation, reaction with a coupling reagent and/or reaction with a compound having two or more functional groups. The drug can be loaded into or onto the spherical particle, either simultaneously with the preparation of the carrier system or sequentially, by the addition of a suspension of spherical particles to an appropriate drug solution. The preparation is said optionally to comprise the addition of 0.1 to 2% of a surfactant.

EP-A-0877033 describes a reverse micelle emulsion cross-linked polymerisation reaction to produce particles up to 100 nm. The polymerized reaction product is dried to remove solvent and the dried particles dispersed in an aqueous buffer. Surfactant and other toxic materials are then separated from the particles.

WO 96/25919 describes an aerosol comprising droplets of an aqueous dispersion of nanoparticles. The nanoparticles comprise beclomethazone particles having a surface modifier on the surface thereof. The beclomethazone nanoparticles can be prepared by grinding or a micro-precipitation method.

EP-A-0274431 describes forming a mixture of one or more surface-active agents, water and one or more physiologically active compounds and emulsifying the mixture by means of a colloid mill and/or micro fluidiser to produce a two phase coacervate composition.

It is an object of the present invention to provide a particulate composition in a dry state comprising nanoparticles which composition provides an improvement over the prior art.

It is a further object of the present invention to provide a method for preparing a particulate composition.

It is a further object of the present invention to provide an aerosol composition comprising the particulate composition of the present invention and an aerosol liquid propellant.

According to a first aspect of the present invention there is provided a particulate composition comprising particles, wherein the said particles:
(a) include an active material and, with respect to the total weight of the particles, more than 2 wt % of a surfactant material;
(b) have an average diameter of more than about 1 nm and less than about 1000 nm;
(c) are spheroidal or spherical in shape; and
(d) contain no cross-linked polymer formed from a monomer or preformed polymer with a cross-linking agent and initiator.

Preferably the active material is a medicament.

According to a further aspect of the present invention there is provided an aerosol composition comprising a liquid aerosol propellant and the present particulate composition.

The aerosol composition can be in a form suitable for oral inhalation, nasal and/or ocular administration to a patient.

The surfactant material contained in the present particulate composition can determine the surface properties of the particles. In particular, the choice of surfactant material can permit the exterior surface of the particles to be tailored to a specific application.

For example, when contained in an aerosol composition the surfactant material contained in the present particulate composition can aid dispersion of the particles throughout the liquid propellant.

The nanometer size or less of the present particles permits delivery in the form of an oral or nasal aerosol inhaler to the lower pulmonary tissues, including the alveoli and lower airways.

The presence of the surfactant in the present particulate composition can ensure a smooth exterior surface to the particles.

The absence in the particles of the present particulate composition of cross-linked polymer formed using a cross-linking agent and initiator ensures the absence of any residual monomer, preformed polymer, cross-linking agent or initiator. Any such residues are inevitably present in a cross-linked polymer product formed using cross-linking agent and initiator, albeit, in small amounts, and are potentially toxic in in vivo applications and capable of adversely affecting the stability of the medicament.

The present particles preferably comprise a core material including the active material and a coating on the core material comprising the surfactant material.

Preferably the particulate composition comprises particles in which the core material is hydrophilic and is surrounded by surfactant coating. Such particulate compositions having a hydrophilic core would be particularly suitable for the production of peptide, nucleic acid and/or protein-containing particles. Some such systems may be suitable for inhalation, particularly from metered dose inhalers.

Alternatively, however, the particulate composition can comprise particles in which the core material is hydrophobic and is surrounded by surfactant coating. Such an arrangement can provide a useful vehicle for the oral delivery of lipophilic poorly soluble drugs, which can show low absorption due to their slow dissolution rate. Inclusion of such drugs in the present particulate composition with a lipophilic core can show an increased dissolution rate. Some such systems may be suitable for inhalation, particularly from metered dose inhalers.

Preferably the particles have an average diameter within the range of from about 1 nm up to less than about 1000 nm. More preferably, the particles have an average diameter within the range of from about 10 nm to about 800 nm, even more preferably within the range of from about 20 nm to about 400 nm.

For use in an aerosol composition intended for deep lung delivery of a medicament, the present particulate composition ideally comprises particles having an average diameter within the range of from about 1 nm up to less than about 1000 nm.

Throughout the present specification, by the term "average diameter" is meant the mean diameter calculated from photon spectroscopy measurement.

Preferably the particles of the present particulate composition comprise, with respect to the total weight of the particles, up to about 90 wt % surfactant material, more preferably up to about 80 wt % surfactant material, even more preferably up to about 60 wt % surfactant material. The particles preferably comprise more than about 10 wt %, more preferably more than about 20 wt %, even more preferably more than about 30 wt % surfactant material, with respect to the total weight of the particles. The actual amount of surfactant material selected will be dependent on the particular benefits which it is desired to confer on the resultant dry particles.

The surfactant material employed can be selected from the group comprising ionic (including anionic and cationic), nonionic, zwitterionic and amphoteric surfactants and mixtures thereof. Throughout the present specification the term "surfactant" includes within its scope "emulsifier". The surfactant may also include a co-surfactant. Suitably a surfactant for use in the present invention is selected from the group comprising phospholipids; sorbitan esters (some of which are known as SPANs); poloxamers; polyoxyethylene sorbitan esters (some of which are known as TWEENs); polyoxyethylene esters (some of which are known as Brij); bile salts; sodium bis (2-ethylhexyl) sulphosuccinate (available commercially as Aerosol OT and known as AOT); and mixtures thereof. If desired, co-surfactant can be included for the surfactant selected.

A preferred surfactant for use in an aerosol composition is lecithin in combination with propan-2-ol at a weight ratio of lecithin to propan-2-ol in the range of from 1:3 to 1:10, preferably at a weight ratio of 1:3.

The present particulate composition can provide particles in a dry state, by which is meant a particulate material that feels dry to touch and flows as a powder.

Where the active material present in the particulate composition is a medicament it can be any medicament that can usefully be delivered in the form of particles having a size of from about 1 nm up to about 1000 nm.

Medicaments appropriate for delivery in the form of an aerosol composition intended for use as an inhaler include medicaments for use in the treatment and prevention of asthma and other conditions associated with reversible airways obstruction. Such medicaments either alone or in any combination can be selected from the group comprising:

(i) salbutamol, salbutamol sulphate, mixtures thereof and physiologically acceptable salts and solvates thereof, (ii) terbutaline, terbutaline sulphate, mixtures thereof and physiologically acceptable salts and solvates thereof, (iii) beclomethasone dipropionate and physiologically acceptable solvates thereof, (iv) budesonide and physiologically acceptable solvates thereof, (v) triamcinolone acetonide and physiologically acceptable solvates thereof, (vi) ipratropium bromide and physiologically acceptable salts and solvates thereof, (vii) corticosteroid or bronchodilator, and (viii) leukotriene antagonists.

Other examples of particulate medicaments suitable for oral or nasal inhalation by means of the present aerosol composition include:

(ix) peptides, proteins, nucleic acids and derivatives thereof for use in the treatment and prevention of disease states; and (x) insulin, calcitonin, growth hormone, lutenising hormone release hormone (LHRH), leuprolide, oxytocin and physiologically acceptable salts and solvates thereof for use in the treatment and prevention of disease states including diabetes.

Further examples of appropriate medicaments which can be formed into the present particulate compositions may additionally be selected from, for example, analgesics, e.g., codeine, dihydromorphine, ergotamine, fentanyl or morphine; anginal preparations, e.g., diltiazem; antiallergics, e.g., cromoglycate, ketotifen or nedocromil; anti-infectives e.g., cephalosporins, penicillins, streptomycin, sulphonamides, tetracyclines and pentamidine; antihistamines, e.g., methapyrilene; antiinflammatories, e.g., beclomethasone dipropionate, fluticasone propionate, flunisolide, budesonide, rofleponide, mometasone furoate or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenyipropanolamine, pirbuterol, reproterol, rimiterol, terbutaline, isoetharine, tulobuterol, or (−)4-amino-3,5-dichlor-α[[[6-[2-(2-pyridinyl)ethoxy]hexyl]methyl]benzenemethanol; diuretics, e.g., amiloride; anticholinergics, e.g., ipratropium, tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon. It will be clear to a person skilled in the art that, where appropriate, the medicaments may be used in the form of salts, (e.g., as alkali metal or amine salts or as acid addition salts) or as esters (e.g., lower alkyl esters) or as solvates (e.g., hydrates) to optimise the activity and/or stability of the medicament.

Preferred medicaments are selected from salbutamol, salmeterol, fluticasone propionate and beclomethasone dipropionate and salts or solvates thereof, e.g., the sulphate of albuterol and the xinafoate of salmeterol.

Medicaments can also be delivered in combinations. Preferred formulations containing combinations of active ingredients contain salbutamol (e.g., as the free base or the sulphate salt) or salmeterol (e.g., as the xinafoate salt) in combination with an anti-inflammatory steroid such as a beclomethasone ester (e.g., the dipropionate) or a fluticasone ester (e.g., the propionate).

Examples of nucleic acid systems include corrective plasmid DNA (pDNA) constructs capable of expressing a therapeutic gene. Preferred nucleic acid systems are pDNA constructs whose stability and activity have been enhanced by pre-condensation with a polycationic peptide, for example, a protamine such as protamine sulphate. Suitably any protamine is included at a concentration of 0.1 to 10 mg/mg, more suitably 0.8 to 2 mg/mg, with respect to the nucleic acid.

The dosage requirements for any one medicament will be those conventionally employed in, for example, inhalers.

For example, where the active material is salbutamol for use in relation to asthma the inhaler is employed as required, usually 1 or 2 actuations (i.e. puffs) between 0 and 4 times per day, with a single metered dose comprising 100 micrograms of salbutamol in a volume of metered liquid propellant between 20 and 150 µl.

If desired, the particles of the present particulate composition can include material in addition to the active material and the surfactant material. Such additional material can act as a matrix or carrier. Preferably the weight ratio of the active material to any additional material present in the particles, other than the surfactant material, lies within the range of from about 99:1 to about 1:99. More preferably such a ratio lies within the range from about 99:1 to about 20:80

Suitably, such an additional material can be a polymeric material. Preferably such a polymeric material has a molecular weight within the range of from about 250 to about $10 \times 10^6$ daltons. The presence of a polymeric material in a particulate composition can permit, for example, the sustained and controlled release of the active material once, for example, the particulate composition has been administered to a patient. Suitable examples of such polymeric materials include polyacrylic acid; chitosan; polylactic-glycolic acid; polylactic acid; albumin; and hyaluronic acid. One or more than polymeric material can be included in order to give the desired properties.

Preferably the weight ratio of the active material such as a medicament to the total amount of polymeric material present lies within the range of from about 99:1 to about 1:99, more preferably within the range of from about 99:1 to about 20:80.

A further example of an additional material that can beneficially be included in the particles comprising the present particulate composition is a sugar. The sugar may be present with or without the polymeric material.

Examples of suitable sugars include mono and/or disaccharides, such as for example lactose, sucrose and trehalose. The inclusion of a sugar in the present particles can confer stability on the active material during processing and storage of the particulate composition. Examples of active materials whose stability may be increased in the presence of sugar include nucleic acid, peptide and/or protein based drugs. Sucrose is particularly preferred for use with nucleic acids.

The weight ratio of the active material such as a medicament to any sugar present in the particles preferably lies within the range of from about 99:1 to about 1:99, more preferably from about 99:1 to about 20:80.

Further examples of additional materials that can beneficially be included in the present particles, particularly when the active material is a nucleic acid and the particulate composition is intended to be used as an aerosol composition, include one or more cationic lipids as they may facilitate cellular entry of genetic material and a peptide to protect the nucleic acid. An example of a suitable cationic lipid is 1,2-dioleoyl-3-trimethylammonium propane (DOTAP).

Any additional material present is suitably in the form of a matrix incorporating the active material.

The present particulate composition can thus provide nanoparticles, as well as particles less than 1 nm in diameter, comprising an active material, such as a drug, as a major part of the particle. Where the surfactant material is in the form of a coating, the active material in the form of, for example, a medicament can comprise 100 wt % of the core material.

In an aerosol composition according to the present invention, the liquid propellant can be selected from the group comprising hydrocarbons, hydrochlorocarbons, chlorocarbons, hydrochlorofluorocarbons, hydrofluorocarbons, fluorocarbons and mixtures thereof. Hydrofluorocarbons and fluorocarbons are preferred having regard to environmental considerations and local legislative requirements. Preferred propellants for use in an aerosol composition intended for administration to a patient include hydrofluoroalkanes selected from the group comprising 1,1,1,2-tetrafluoroethane, 1,1,1,2,3,3,3-heptafluoropropane and mixtures thereof, optionally in combination with a minor proportion of n-alkane, for example n-hexane.

Suitably the aerosol composition comprises an aerosol liquid propellant and the particulate composition at a weight ratio of liquid propellant to particulate composition within the range of from about 10,000:1 to about 25:1, more preferably within the range of from about 1,000:1 to about 100:1. Additional ingredients can be included in the aerosol composition if desired.

Preferably the aerosol composition is supplied in the form of a metered dose inhaler.

According to a further aspect of the present invention there is provided a metered dose inhaler containing the aerosol composition of the present invention.

The metered dose inhaler can be prepared by conventional manufacturing methods. For example, under the appropriate pressure the particulate composition and the liquid propellant can be admixed in bulk, dosed into the container of an inhaler and sealed under a pressure of between about 689.476 Pa (10 psig) and about 8273.712 Pa (120 psig). Alternatively, the particulate composition, if desired dispersed in an organic liquid at a preferred weight ratio of particles to organic liquid within the range of about 1:10 to about 1:100, and the liquid propellant can be dosed separately to the container of an inhaler prior to sealing under pressure. The appropriate dosing and metering valve can, in either instance, then be inserted.

According to a further aspect of the present invention the aerosol composition of the present invention is provided for use in the administration of the deep lung delivery of a medicament to a patient in need thereof.

Such a mode of administration can be employed to treat respiratory disease, such as for example asthma, and/or to deliver a medicament to be absorbed systemically by the patient. Examples of medicaments beneficially delivered by deep lung systemic absorption include medicaments containing a nucleic acid, a peptide and/or a protein. Medicaments for deep lung delivery containing a peptide and/or a protein, such as for example insulin, are employed to treat, for example, diabetes. Medicaments for deep lung delivery containing a nucleic acid, such as for example pDNA constructs for expression of corrective proteins, immunostimulatory proteins and enzymes, ribonucleic acids and antisense oilgonucleotides, can be employed to treat, for example, cystic fibrosis and cancer.

According to a further aspect of the present invention there is provided the use of the present particulate composition in the manufacture of an aerosol composition for the lung delivery of a medicament for the treatment of, for example, respiratory disorders in a patient.

According to a further aspect of the present invention there is provided a method of administering a particulate composition to a patient in need thereof comprising spraying the aerosol formed from the aerosol composition of the present invention on to or towards the area intended to receive the particulate composition.

Where the aerosol composition is in a form intended for oral or nasal application, the method includes the patient inhaling the particulate composition.

According to a further aspect of the present invention there is provided a method for preparing a particulate composition comprising particles having an average diameter within the range of from about 1 nm up to less than about 1000 nm, wherein the method comprises:
(i) forming a colloidal system comprising a continuous phase and micelles, the micelles comprising surfactant material;
(ii) forming a microemulsion by admixing the colloidal system of step (i) with a solution comprising an active material dissolved in a solvent, wherein the solution forms a disperse phase within the micelles of surfactant material;
(iii) quenching at least the disperse phase to a solid state; and
(iv) removing the continuous phase and the solvent so as to yield the said particles.

Preferably step (iii) includes snap freezing the continuous phase and the disperse phase, suitably in liquid nitrogen. The continuous phase and the disperse phase can be removed by freeze-drying, otherwise known as lyophilising.

Alternatively, steps (iii) and (iv) can include quenching the disperse phase to a temperature higher than the freezing point of the continuous phase, separating, for example by centrifugation or ultrafiltration, the solidified disperse phase and the liquid continuous phase, and removing by freeze-drying the solvent from the disperse phase.

Preferably the continuous phase is an apolar liquid and the solvent is water. Suitably the apolar liquid is a hydrocarbon, preferably selected from the group comprising iso-octane, octane, heptane, hexane, cyclohexane and mixtures thereof. The combination of an apolar solvent and an aqueous solution contained within reverse micelles (known as $L_2$ micelles) of surfactant material can yield particles comprising a hydrophilic core material containing the active material and a coating comprising the surfactant material.

Alternatively, the solvent can comprise a lipophilic compound-solubilising liquid or a liquid miscible with a lipophilic compound, and the continuous phase comprises a liquid immiscible with the solvent, such as an aqueous based phase. The combination of an aqueous based continuous phase and a lipid containing disperse phase contained within normal micelles (known as $L_1$ micelles) can yield particles comprising a hydrophobic core material containing the active material and a coating comprising the surfactant material.

The surfactant material is suitably selected from the group comprising anionic, cationic, nonionic, zwitterionic, amphoteric surfactants and mixtures thereof. As explained above, the surfactant material can be an emulsifier and the surfactant material can include a co-surfactant. Suitable and preferred surfactants are those set out above.

Preferably, the colloidal system formed in step (i) comprises a weight ratio of continuous phase to surfactant material within the range of from about 10,000:1 to about 30:70, preferably within the range of from about 100:1 to about 40:60.

Preferably the solution of active material of step (ii) is at a concentration of about 2,000 to about 0.1 μg/g, more preferably about 2,000 to about 0.1 mg/g, active material in the solvent. The lower levels of concentration of the active material may be suitable for use when the active material is a nucleic acid.

Preferably the colloidal system of step (i) is admixed with the solution of step (ii) at a weight of colloidal system to solution within the range of from about 45:55 to about 100:1, preferably within the range of from about 60:40 to about 95:5.

The solution of step (ii) can include dissolved material additional to the said active material. The additional material can be included in the solution at a concentration of from about 2000 to about 0.1 mg/g, preferably at a concentration of from about 1500 to about 10 mg/g, with respect to the solvent. As explained above, the additional material may be suitably selected from the group comprising non-cross linked polymeric materials, sugars, other beneficial ingredients, such as, for example, cationic lipids and peptides, and mixtures thereof. Where the active material includes a nucleic acid a polycationic peptide, such as for example protamine sulphate may suitably be included at a concentration of from about 0.1 to about 10 mg/mg, preferably 0.8 to 2 mg/mg, with respect to the nucleic acid. The nucleic acid is suitably pre-condensed with the polycationic peptide. The cationic lipid is preferably 1,2-dioleoyl-3-trimethylammonium propane and can usefully be included when the active material is a nucleic acid.

The active material can be a medicament. The medicament can be any of those mentioned above, the solvent being selected to dissolve the medicament chosen.

The present method can be employed to prepare the particulate composition of the present invention. The formation of the disperse phase within the micelles of the surfactant material ensures that the finished particles have a spheroidal or spherical shape.

The particulate composition product of the present method can be employed in the preparation of the present aerosol composition, in the present use in the manufacture of an aerosol composition for lung delivery of a medicament for the treatment of, for example, a respiratory disorder in a patient, and in the present method of administering a particulate composition to a patient in need thereof comprising spraying the aerosol formed from the present aerosol composition on to or towards the area intended to receive the particulate composition.

If desired the particles formed by the present method can be washed to reduce their content of surfactant material.

Embodiments of the present invention will now be described, by way of example only, with reference to the following examples and the accompanying drawings, wherein:

FIG. 1 is a ternary phase diagram of an AOT/aqueous/iso-octane system at 20° C.;

FIG. 2 is a scanning electron micrograph of particles embodying the present invention;

FIG. 3 is a ternary phase diagram of a lecithin:propan-2-ol 1:3/aqueous/iso-octane system at 20° C.;

FIG. 4 is a scanning electron micrograph of particles embodying the present invention;

FIG. 5 is a vertical cross section of a metered dose inhaler; and

FIG. 6 is a vertical cross section of the spring mechanism of the metered dose inhaler of FIG. 5.

GENERAL EXPERIMENTAL PROCEDURES

Construction of Ternary Phase Diagrams

Water-in-iso-octane microemulsions were produced by adding filtered distilled water to a surfactant/iso-octane solution. Each mixture was gently agitated with a bench vortex for several seconds and then allowed to stand for 15 minutes to ensure equilibrium of the mixture. Water addition was successively repeated to determine the phase boundary between the crystal clear micellar phase and the opaque multiphase of the system.

Figure 1:
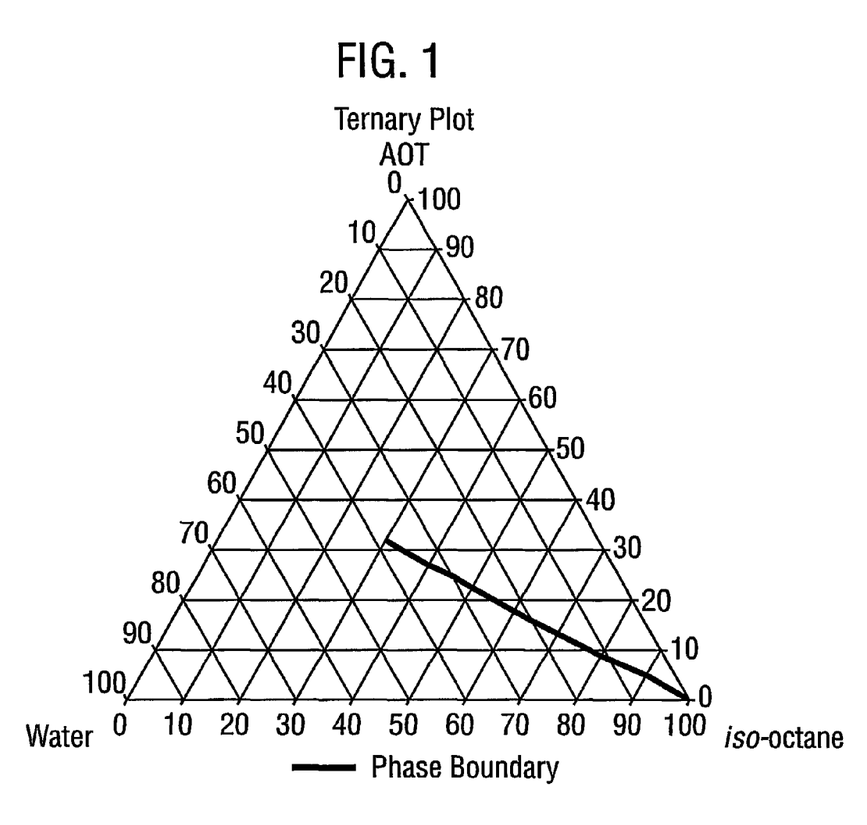

Following the above experimental procedure a ternary phase diagram was constructed for the ternary system of water/sodium bis (2-ethylhexyl) sulphosuccinate/iso-octane at 20° C. The phase diagram is shown in FIG. 1. AOT stands for Aerosol OT, which is the name for a commercially available sample of sodium bis (2-ethylhexyl) sulphosuccinate. Compositions to the right of the phase boundary line shown in FIG. 1 are in the form of water-in-iso-octane microemulsions.

Figure 3:
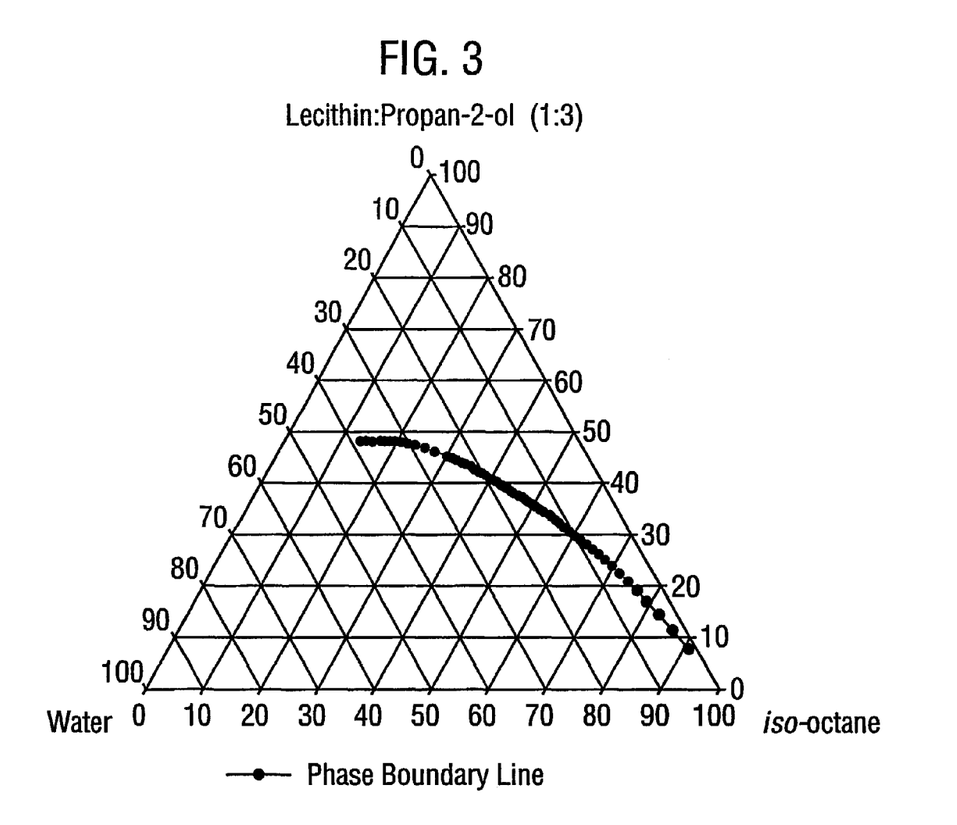

Following the above experimental procedure a ternary phase diagram was constructed for the ternary system of water/lecithin:propan-2-ol(1:3 by weight)/iso-octane. The phase diagram is shown in FIG. 3. Compositions to the right of the phase boundary line shown in FIG. 3 are in the form of water-in-iso-octane microemulsions.

EXAMPLES

A drug, with or without a matrix, was dissolved in water. The resulting solution was added to the selected surfactant/iso-octane colloidal system to give a final aqueous phase comprising 1 to 30% by weight of the total emulsion composition.

The microemulsion drug-containing composition was snap frozen by submersion in liquid nitrogen.

The product was freeze-dried at −55° C. to remove the iso-octane and the water.

Particle Size Analysis

Particles produced were dispersed in filtered iso-octane and sonicated for 3 minutes, transferred to a quartz cuvette and sealed to prevent iso-octane evaporation. The cuvette was inserted in a Coulter N4 plus to measure the size of the particles. Multimodal analysis was performed using the Coulter N4 plus standard distribution processor technology. Particle size analysis was repeated for n>7.

Scanning Electron Microscopy (SEM) of Nanoparticles

Excess surfactant was removed by washing the particles with iso-octane using centrifugation. The resulting nanoparticles were dried under a nitrogen stream and splutter layered with gold. Scanning electron micrographs of the resulting nanoparticles were taken using a Philips XL 20 SEM.

HPLC Assay of Salbutamol Sulphate

Salbutamol sulphate concentrations were determined using reverse phase HPLC (high pressure liquid chromatography). A $C_{18}$ column was employed at ambient temperature with detection at 278 nm. The mobile phase consisted of a methanol:water phase at a ratio of 55:45 v/v, containing heptane sulphonic acid 1.1013 g/l and adjusted to pH 3.0 with glacial acetic acid. The mobile phase was passed through the column at a flow rate of 1 mL/min.

Samples were prepared using a standard solution of 600 mL of ethanol made up to 1000 mL with water, and containing bamethane 7 µgm $L^{-1}$.

Metered Dose Inhaler

Figure 5:
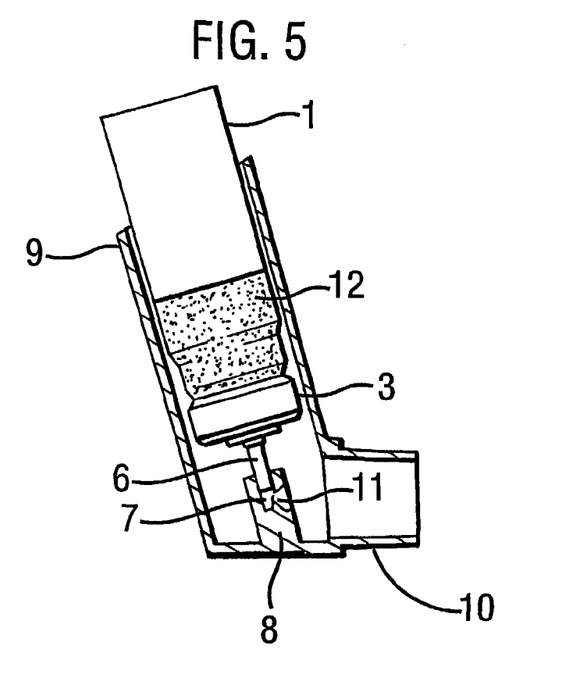
Figure 6:
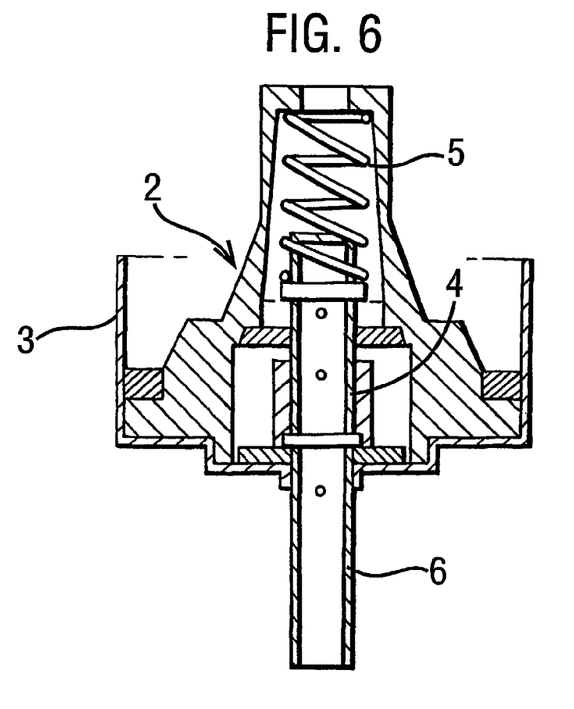

Aerosol compositions were dosed into the metered dose inhaler illustrated in FIGS. 5 and 6. The metered dose inhaler comprises an inverted container (1) and a metering valve (2). The inverted container (1) is capable of withstanding a pressure up to $6.895 \times 10^5$ Pa (100 psig) and is closed by a closure cap (3). The metering valve (2) extends through the closure cap (3) and includes a fixed volume chamber (4), a spring mechanism (5) biased to maintain the valve closed when not being actuated and an outlet stem (6) which opens into an expansion chamber (7). The container (1) and metering valve (2) are mounted by support (8) in a holder (9) which is integral with an actuator tube (10) extending at an obtuse angle away from the holder (9). As can be seen in the drawing the expansion chamber (7) opens by way of a spray jet orifice (11) into the actuator tube (10). The container (1) contains the aerosol composition (12) comprising propellant and the particulate composition.

In use the container (1) is depressed relative to the holder (9) causing the chamber (4) to open to the atmosphere and the fixed volume of liquefied gas therein to expand forcing the composition into the expansion chamber (7) where the liquefied gas continues to expand and evaporate. The actuator tube (10) directs the aerosol.

Example 1

A microemulsion composition was prepared following the above procedure from 78% w/w iso-octane, 6% w/w sodium bis (2-ethylhexyl) sulphosuccinate, and 16% w/w of an aqueous phase. The aqueous phase comprised, with respect to the aqueous phase, 0.06% w/w bromothymol blue and 17.17% w/w polyacrylic acid (molecular weight 2000), with the balance being water.

The size of the resulting particles was measured using the photon correlation spectroscopy technique described above employing the Coulter N4. The particles were found to be 232±58 nm, n=7 mean±sd.

Figure 2:
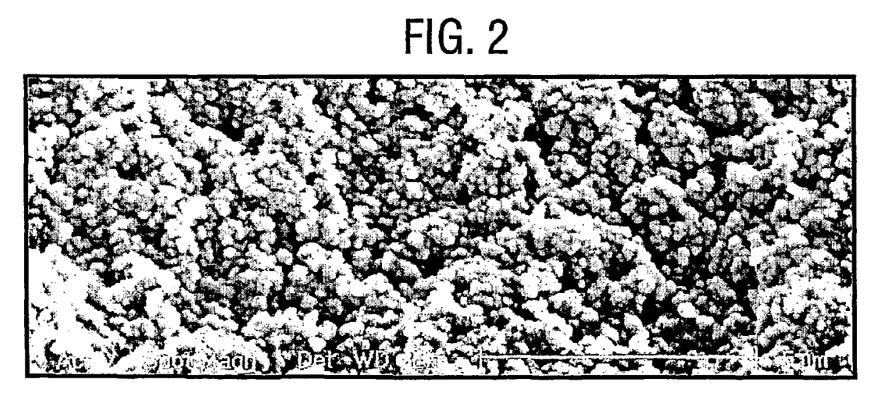

The particles were also subjected to scanning electron microscopy employing the procedure described above. FIG. 2 is the scanning electron micrograph of the present particles. The particles appear spherical and to have a diameter of approximately 250 nm, which is in line with the data from the photon correlation spectroscopy sizing data.

Example 2

Microemulsion compositions were prepared following the above procedure for three compositions comprising iso-octane, lecithin:propan-2-ol(1:3 w/w) and an aqueous phase. The relative proportions of each phase and the content of the aqueous phase are given in Table I below.

TABLE I

| Formulation | Iso-octane (% w/w) | Surfactant (% w/w) Lecithin: Propan-2-ol (1:3) | Aqueous Phase (% w/w)/composition |
|---|---|---|---|
| B | 25 | 45 | 30/salbutamol sulphate (17% w/v) |
| C | 35 | 45 | 20/salbutamol sulphate (17% w/v) |
| D | 40 | 40 | 20/salbutamol sulphate:lactose (70:30) (17% w/v) |

The size of the resulting particles formed from each formulation was measured by photon correlation spectroscopy employing the Coulter N4 machine in the above described procedure. The results are given in Table II below.

TABLE II

| Formulation | Nanoparticle size by PCS (scattering intensity) (mean ± sd, n = 7) |
|---|---|
| B | Population 1 (50.4%): 216 ± 43 nm |
|   | Population 2 (49.6%):  40 ± 15 nm |
| C | 34 ± 17 nm |
| D | 69 ± 39 nm |

Figure 4:
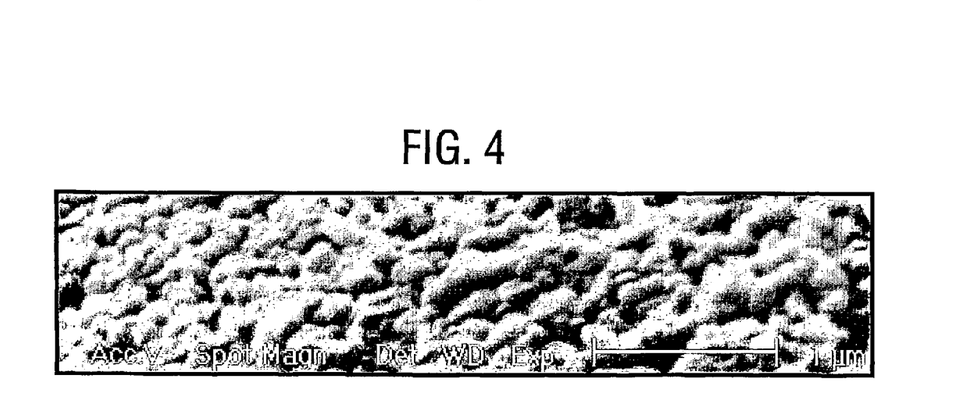

A scanning electron micrograph of the salbutamol sulphate nanoparticles resulting from Formulation B was measured using the procedure described above. FIG. 4 is a representation of the resulting scanning electron micrograph. The particles shown in FIG. 4 appear spherical and generally less than 100 nm in size in keeping with the measurements given in Table II.

Example 3

Each of the nanoparticles resulting from the ternary formulations of Example 2 was employed to produce an aerosol composition.

In each case ~30 mg of nanoparticles were dispersed in 0.5 g n-hexane with 3 minutes sonication in a plastic vial for use in a pressurised metered dose inhaler. A Bespak BK 357 100 µL metering valve was crimped in place and hydrofluoroalkane propellant (14 g HFA-227) was added using a pressure burette. The valve was actuated through a mouthpiece with a 0.25 mm orifice.

Visual evaluation of the compositions was performed prior and subsequent to sonication and at later time points to assess formulation stability and homogeneity.

The aerosol performance of each resulting nanoparticle HFA formulations was assessed by cascade impaction. The plates of an Andersen cascade impactor were coated with polyethylene glycol (molecular weight 300) to reduce particle bounce and re-entrainment.

In each case the pressurised metered dose inhaler was primed by firing five shots to waste and then 20 actuations were introduced into the Andersen cascade impactor, operating at 28.3 L min$^{-1}$, via a BP two-stage liquid impinger inlet. The actuator, inlet, impactor stages and filter were washed with 10 mL solution of a 50% ethanol/50% water mixture by sonication in a polythene bag.

Each washing was assayed for salbutamol sulphate concentration by HLPC-UV according to the procedure described above.

The results in terms of fine particle fraction, mass median aerodynamic diameter (MMAD) and geometric standard deviations (GSD) of the aerosols produced are given in Table III below. Three batches of each nanoparticle were employed to give the present results (mean±sd, n=5).

TABLE III

| Formulation | Fine Particle Fraction (ex device, <5.8 µm) (%) | MMAD (µm) | GSD (µm) |
|---|---|---|---|
| B | 58.3 ± 6.8 | 1.2 ± 0.4 | 2.3 ± 1.1 |
| C | 65.5 ± 5.1 | 1.3 ± 0.2 | 2.3 ± 0.3 |
| D | 59.0 ± 4.6 | 1.5 ± 0.6 | 1.9 ± 0.8 |
| Model | 88.0 ± 8 | 1.14 ± 0.03 | 2.12 ± 0.05 |

Included in Table III are equivalent data for a model solution system comprising a mixture of 30 mg hexyl biphenylacetate, 0.5 g n-hexane and 14 g HFA-227. The data with respect to nanoparticles of the present invention are comparable to that of the model system. The model system represents the optimum that could be achieved with the present apparatus.

The fine particle fraction is the fraction likely to get into the lungs. The fine particle fraction for each of formulation B, C and D compares well to that achieved using the model solution.

The MMAD is an indication of the potential deposition site in the lungs. For each of formulations B, C and D, as well as the model system, the relatively low MMAD recorded suggests deep lung deposition.

The GSD is an indication of the polydispersity of the aerosols produced.

The combination of high fine particle fraction and low MMAD indicates very good performance of the aerosols. The present data suggests that in use a high fraction of nanoparticles would be deposited within the lung with the deposition being mainly alveolar.

Each of formulations B, C and D comprising nanoparticles produced from the lecithin-based microemulsion and the HFA-227:hexane blend could, on visual evaluation in the plastic vial of the metered dose inhaler, be seen to be in the form of a stable dispersion. Each formulation appeared as a very fine homogeneous dispersion. The presence of a dispersion suggests that some flocculation of the nanoparticles within the hexane/HFA blend had occurred. By contrast, the nanoparticles on dispersion in n-hexane alone produced an optically clear system.

No sedimentation or creaming of the flocculation in the EFA-227/n-hexane blend was observed over several months. The absence of sedimentation and creaming suggests that the flocculated particles must have been less than 1 µm in size, and is desirable in order to ensure reproducible dosing.

The flocculation in the HFA-227/hexane system was removed on aerosolisation, as can be seen from the results recorded in Table III for formulations B, C and D, relative to the model system.

By comparison, it proved impossible to disperse the product of Example 1 above in an HFA propellant. Even with the inclusion of a co-solvent for the AOT/iso-octane at a level of up to 10% w/w the nanoparticles aggregated and adsorbed on the wall of the pressurised metered dose inhaler vial.

Example 4

Nanoparticles were formed using the lecithin:propanol-2-ol 1:3 by weight surfactant system of Example 2 including as the active material pEGFP-N1 reporter plasmid DNA (4700 base pairs). The particles also contained protamine sulphate (1:1 by weight with respect to pDNA) and sucrose at a concentration of 0.5M in the aqueous phase.

Nanoparticle formation was confirmed by photon correlation spectroscopy.

The invention claimed is:

1. A method for preparing a particulate composition comprising particles having an average diameter within the range of from about 1 nm to less than about 1000 nm, wherein the method comprises:
   (i) forming a colloidal system comprising a continuous phase and micelles, the micelles comprising surfactant material;
   (ii) forming a microemulsion by admixing the colloidal system of step (i) with a solution of a medicament dissolved in a solvent, wherein the solution forms a disperse phase within the micelles of surfactant material;

(iii) quenching at least the disperse phase to a solid state; and (iv) removing the continuous phase and the solvent so as to yield the particles.

2. The method according to claim 1 wherein step (iii) comprises snap freezing the continuous phase and the disperse phase.

3. The method according to claim 2 wherein the snap freezing occurs in liquid nitrogen.

4. The method according to claim 1 wherein the continuous phase and the solvent are removed by freeze-drying.

5. The method according to claim 1 wherein steps (iii) and (iv) comprise quenching the disperse phase to a temperature higher than the freezing point of the continuous phase, separating the solidified disperse phase and the continuous phase, and removing the solvent from the disperse phase by freeze drying.

6. The method according to claim 5 wherein the solidified disperse phase is separated from the continuous phase by centrifugation or ultrafiltration.

7. The method according to claim 1 wherein the continuous phase is an apolar liquid and the solvent is water.

8. The method according to claim 7 wherein the apolar liquid is a hydrocarbon.

9. The method according to claim 8 wherein the hydrocarbon is selected from the group consisting of iso-octane, octane, heptane, hexane, cyclohexane, benzene and mixtures thereof.

10. The method according to claim 1 wherein the solvent comprises a lipophilic compound-solubilising liquid or a liquid miscible with a lipophilic compound and the continuous phase comprises a liquid immiscible with the solvent.

11. The method according to claim 1 wherein the surfactant material is selected from the group consisting of emulsifiers, anionic surfactants, cationic surfactants, nonionic surfactants, zwitterionic surfactants, amphoteric surfactants and mixtures thereof.

12. The method according to claim 11 wherein the surfactant material is selected from the group consisting of phospholipids, sorbitan esters, poloxamers, polyoxyethylene sorbitan esters, polyoxyethylene esters, sodium bis(2-ethylhexyl) sulphosuccinate, bile salts and mixtures thereof.

13. The method according to claim 1 wherein the colloidal system formed in step (i) comprises a weight ratio of continuous phase to surfactant material from about 10,000:1 to about 30:70.

14. The method according to claim 1 wherein the solution of a medicament of step (ii) is at a concentration of about 2,000 to about 0.1 µg/g medicament in the solvent.

15. The method according to claim 1 wherein the colloidal system of step (i) is admixed with the solution of step (ii) at a weight ratio of colloidal system to solution from about 45:55 to about 100:1.

16. The method according to claim 1 wherein the solution of step (ii) further comprises dissolved material additional to the medicament.

17. The method according to claim 16 wherein the additional dissolved material is selected from the group consisting of polymeric materials, sugars, cationic lipids, peptides and mixtures thereof.

18. The method according to claim 16 wherein the additional dissolved material is present in the solution at a concentration of about 2,000 to about 0.1 mg/g with respect to the solvent.

19. The method according to claim 1 wherein the medicament is selected from the group consisting of salbutamol, salbutamol sulphate, terbutaline, terbutaline sulphate, ipratropium bromide or any physiologically acceptable salts or solvates thereof; beclomethasone diproprionate, budesonide, triamcinolone acetonide of any physiologically acceptable solvates thereof; corticosteroid, bronchodilator; peptides, proteins, nucleic acids or derivatives thereof; insulin, calcitonin growth hormone, lutenising hormone releasing hormone, leuprolide, oxytocin or any physiologically acceptable salts or solvates thereof; or any mixture thereof.

20. The method according to claim 1 for preparing a particulate composition comprising particles, wherein the particles:

(a) include a medicament and, with respect to the total weight of the particles, from about 2 to about 90 wt % of a surfactant material;

(b) have an average diameter of more than about 1 nm and less than about 1000 nm;

(c) are spheroidal or spherical in shape; and (d) contain no cross-linked polymer formed from a monomer or preformed polymer with a cross-linking agent and initiator.

* * * * *